US005986177A

United States Patent [19]

Osman et al.

[11] Patent Number: 5,986,177

[45] Date of Patent: Nov. 16, 1999

[54] *BACILLUS THURINGIENSIS* ISOLATES WITH BROAD SPECTRUM ACTIVITY

[75] Inventors: Yehia A. Osman, Mansoura; Magdy A. Madkour, Giza, both of Egypt; Lee A. Bulla, Jr., Laramie, Wyo.

[73] Assignees: Agricultural Genetic Engineering Research Institute, Giza, Egypt; University of Wyoming, Laramie, Wyo.

[21] Appl. No.: 09/003,217

[22] Filed: Jan. 6, 1998

Related U.S. Application Data

[60] Provisional application No. 60/035,361, Jan. 10, 1997.

[51] Int. Cl.[6] .............................. A01H 5/00; A01H 5/10; C12N 15/32; C12N 15/82

[52] U.S. Cl. .................... 800/302; 435/320.1; 536/23.71

[58] Field of Search .............................. 435/172.3, 320.1, 435/419, 69.1, 468; 536/23.71; 800/205, 250, 279, 301, 302

[56] References Cited

FOREIGN PATENT DOCUMENTS

| | | |
|---|---|---|
| 0537105 | 4/1993 | European Pat. Off. . |
| WO 95/02693 | 1/1995 | WIPO . |
| WO 97/12980 | 4/1997 | WIPO . |

OTHER PUBLICATIONS

Hofte H, et al. "Insecticidal crystal proteins of *Bacillus thuringiensis*." Microbiol. Rev. 53: 242–255, 1989.

Schnepf HE, et al. "*Bacillus thuringiensis* toxins: regulation, activities, and structural diversity." Curr. Opinion Biotech. 6: 305–312, 1995.

Shin et al. "Distribution of Cry V–type Insecticidal Protein Genes in *Bacillus Thuringiensis* and Cloning of Cry V–type Genes from *Bacillus Thuringiensis* subsp. Kurstaki and *Bacillus Thuringiensis* subsp. Entomocidus", *Applied and Environmental Microbiology* 61:2402–2407 (1995).

Chambers et al. "Isolation and Characteriziation of a Novel Insecticidal Crystal Protein Gene from *Bacillus Thuringiensis* subsp. Aizawai", *Journal of Bacteriology* 173:3966–3976 (1991).

Lee et al. "Diversity of Protein Inclusion Bodies and Identification of Mosquitocidal Protein in *Bacillus Thuringiensis* subsp. israelensis", *Biochemical and Biophysical Research Communications* 126:953–960 (1985).

*Primary Examiner*—Lynette R. F. Smith
*Assistant Examiner*—Amy J. Nelson
*Attorney, Agent, or Firm*—Alston & Bird LLP

[57] ABSTRACT

A broad spectrum Bacillus strain is provided which displays activity against at least two orders of insects. Novel proteins active against corn rootworm and nematodes and methods of isolation are additionally provided. Also provided is a purified crystal protein complex isolated from a Bacillus strain that demonstrates insecticidal properties. In addition, the nucleotide and amino acid sequence of the Cry1I gene isolated from this strain is provided.

10 Claims, 9 Drawing Sheets

```
atg aaa cta aag aat cca gat aag cat caa acg ttg tct agc aat gcg     48
Met Lys Leu Lys Asn Pro Asp Lys His Gln Thr Leu Ser Ser Asn Ala
1               5                   10                  15

aag gta gat aaa atc gcg acg gat tca cta aaa aat gaa aca gat ata     96
Lys Val Asp Lys Ile Ala Thr Asp Ser Leu Lys Asn Glu Thr Asp Ile
            20                  25                  30

gaa ttg aaa aat atg aat aat gaa gat tat ttg aga atg tct gag cat     144
Glu Leu Lys Asn Met Asn Asn Glu Asp Tyr Leu Arg Met Ser Glu His
        35                  40                  45

gag agt att gat ccg ttt gtt agt gca tca aca att caa acg ggt att     192
Glu Ser Ile Asp Pro Phe Val Ser Ala Ser Thr Ile Gln Thr Gly Ile
    50                  55                  60

gga att gct ggt aag att ctt ggt act cta ggc gtt cct ttt cct gga     240
Gly Ile Ala Gly Lys Ile Leu Gly Thr Leu Gly Val Pro Phe Pro Gly
65                  70                  75                  80

caa ata gct agc ctc tat agt ttt atc tta ggc gag ctt tgg cct aag     288
Gln Ile Ala Ser Leu Tyr Ser Phe Ile Leu Gly Glu Leu Trp Pro Lys
                85                  90                  95

ggg aaa agt caa tgg gaa atc ttt atg gaa cat gta gaa gcg att att     336
Gly Lys Ser Gln Trp Glu Ile Phe Met Glu His Val Glu Ala Ile Ile
            100                 105                 110

aat cga aaa ata tca act tat gca aga aat aaa gca ctt acg gac ttg     384
Asn Arg Lys Ile Ser Thr Tyr Ala Arg Asn Lys Ala Leu Thr Asp Leu
        115                 120                 125

aaa gga tta gga gat gcc tta gct gtc tac cat gaa tcg ctt gaa agt     432
Lys Gly Leu Gly Asp Ala Leu Ala Val Tyr His Glu Ser Leu Glu Ser
    130                 135                 140

tgg gtt gga aat cgt aat aac act cga gcg agg agt gta gtc aag aac     480
Trp Val Gly Asn Arg Asn Asn Thr Arg Ala Arg Ser Val Val Lys Asn
145                 150                 155                 160

caa tat atc gca tta gaa ctg atg ttt gtt caa aaa cta cct tct ttt     528
Gln Tyr Ile Ala Leu Glu Leu Met Phe Val Gln Lys Leu Pro Ser Phe
                165                 170                 175
```

Figure 5A

```
gca gta tct ggt gag gaa gta cca tta tta ccg ata tat gcc caa gct    576
Ala Val Ser Gly Glu Glu Val Pro Leu Leu Pro Ile Tyr Ala Gln Ala
            180                 185                 190

gcc aat tta cat ttg ttg tta tta aga gat gca tct att ttt gaa aag    624
Ala Asn Leu His Leu Leu Leu Leu Arg Asp Ala Ser Ile Phe Glu Lys
        195                 200                 205

aat ggg gga tta tca gct tca gaa att tca aca ttt tat aac cgt caa    672
Asn Gly Gly Leu Ser Ala Ser Glu Ile Ser Thr Phe Tyr Asn Arg Gln
    210                 215                 220

gtc gaa cga aca aga gat tat tcc tac cat tgt gtg aaa tgg aat aat    720
Val Glu Arg Thr Arg Asp Tyr Ser Tyr His Cys Val Lys Trp Asn Asn
225                 230                 235                 240

aca ggc cta aat aac ttg agg gct aca aat ggc caa agt tgg gtt cgt    768
Thr Gly Leu Asn Asn Leu Arg Ala Thr Asn Gly Gln Ser Trp Val Arg
                245                 250                 255

tat aat caa ttt cgt aaa gat atc gag tta atg gta tta gat tta gtt    816
Tyr Asn Gln Phe Arg Lys Asp Ile Glu Leu Met Val Leu Asp Leu Val
            260                 265                 270

cgc gta ttc cca agc tat gat aca ctt gta tat cct att aaa acc act    864
Arg Val Phe Pro Ser Tyr Asp Thr Leu Val Tyr Pro Ile Lys Thr Thr
        275                 280                 285

tca caa ctt aca aga gaa gta tat aca gac gca att ggg acc gtc gat    912
Ser Gln Leu Thr Arg Glu Val Tyr Thr Asp Ala Ile Gly Thr Val Asp
    290                 295                 300

ccg aat caa gct ctt cga agt acg act tgg tat aat aat aat gca cct    960
Pro Asn Gln Ala Leu Arg Ser Thr Thr Trp Tyr Asn Asn Asn Ala Pro
305                 310                 315                 320

tcg ttc tct gcc ata gag gct gct gtt atc cga agt cca cac cta ctt    1008
Ser Phe Ser Ala Ile Glu Ala Ala Val Ile Arg Ser Pro His Leu Leu
                325                 330                 335
```

Figure 5B

```
gat ttt cta gaa aaa gtt aca att tac agc tta tta agt cgg tgg agt   1056
Asp Phe Leu Glu Lys Val Thr Ile Tyr Ser Leu Leu Ser Arg Trp Ser
            340                 345                 350

aat act cag tat atg aat atg tgg gga gga cat aga ctt gaa tcc cgc   1104
Asn Thr Gln Tyr Met Asn Met Trp Gly Gly His Arg Leu Glu Ser Arg
        355                 360                 365

cca ata gga ggg gca tta aat acc tca aca caa gga tct acc aat act   1152
Pro Ile Gly Gly Ala Leu Asn Thr Ser Thr Gln Gly Ser Thr Asn Thr
    370                 375                 380

tcg att aat cca gta aca tta cag ttc acg tct cga gac ttc tat agg   1200
Ser Ile Asn Pro Val Thr Leu Gln Phe Thr Ser Arg Asp Phe Tyr Arg
385                 390                 395                 400

act gaa tca tgg gca ggg ctg aat tta ttt tta act caa cct gtt att   1248
Thr Glu Ser Trp Ala Gly Leu Asn Leu Phe Leu Thr Gln Pro Val Ile
                405                 410                 415

gga gta cct aga gtt gat ttc cat tgg aaa ttt ccc acg cta cca ata   1296
Gly Val Pro Arg Val Asp Phe His Trp Lys Phe Pro Thr Leu Pro Ile
            420                 425                 430

gca tct gat aat ttt tat tat cta ggg tat gct gga gtt ggt acg caa   1344
Ala Ser Asp Asn Phe Tyr Tyr Leu Gly Tyr Ala Gly Val Gly Thr Gln
        435                 440                 445

tta caa gat tca gaa aat gaa tta cca cct gaa aca aca gga cag cca   1392
Leu Gln Asp Ser Glu Asn Glu Leu Pro Pro Glu Thr Thr Gly Gln Pro
    450                 455                 460

aat tat gaa tca tat agt cat aga tta tcc cat ata gga ctc att tca   1440
Asn Tyr Glu Ser Tyr Ser His Arg Leu Ser His Ile Gly Leu Ile Ser
465                 470                 475                 480

gca tcc cac gtg aaa gca ttg gta tat tct tgg aca cat cgt agt gca   1488
Ala Ser His Val Lys Ala Leu Val Tyr Ser Trp Thr His Arg Ser Ala
                485                 490                 495

gat cgt aca aat aca att gag cca aat agc att aca caa ata cca tta   1536
Asp Arg Thr Asn Thr Ile Glu Pro Asn Ser Ile Thr Gln Ile Pro Leu
            500                 505                 510
```

Figure 5C

```
gta aaa gcg ttc aat ctg tct tca ggt gcc gct gta gtg aga gga cca    1584
Val Lys Ala Phe Asn Leu Ser Ser Gly Ala Ala Val Val Arg Gly Pro
        515                 520                 525

gga ttt aca ggt ggg cat atc ctt cga aga acg aaa tct ggt aca ttt    1632
Gly Phe Thr Gly Gly His Ile Leu Arg Arg Thr Lys Ser Gly Thr Phe
    530                 535                 540

ggg cat ata cga gta aat att aat cca cca ttt gct caa aga tat cgc    1680
Gly His Ile Arg Val Asn Ile Asn Pro Pro Phe Ala Gln Arg Tyr Arg
545                 550                 555                 560

gtg agg atg tcc tat gct tct act aca gat tta caa ttc cat acg tca    1728
Val Arg Met Ser Tyr Ala Ser Thr Thr Asp Leu Gln Phe His Thr Ser
            565                 570                 575

att aac ggt aaa gct att aat caa ggt aat ttt tca gca act atg aat    1776
Ile Asn Gly Lys Ala Ile Asn Gln Gly Asn Phe Ser Ala Thr Met Asn
        580                 585                 590

aga gga gag gac tta gac tat aaa acc ttt aga act gta ggc ttt acc    1824
Arg Gly Glu Asp Leu Asp Tyr Lys Thr Phe Arg Thr Val Gly Phe Thr
        595                 600                 605

act cca ttt agc ttt tca gat gta caa agt aca ttc aca ata ggt gct    1872
Thr Pro Phe Ser Phe Ser Asp Val Gln Ser Thr Phe Thr Ile Gly Ala
    610                 615                 620

tgg aac ttc tct tca ggt aac gaa gtt tat ata ggt cga att gaa ttt    1920
Trp Asn Phe Ser Ser Gly Asn Glu Val Tyr Ile Gly Arg Ile Glu Phe
625                 630                 635                 640

gtt ccg gta gaa gta aca tat gag gca gaa tat gat ttt gaa aaa gcg    1968
Val Pro Val Glu Val Thr Tyr Glu Ala Glu Tyr Asp Phe Glu Lys Ala
            645                 650                 655

caa gag aag gtt act gca ctg ttt aca tct acg aat cca aga gga tta    2016
Gln Glu Lys Val Thr Ala Leu Phe Thr Ser Thr Asn Pro Arg Gly Leu
        660                 665                 670
```

Figure 5D

```
aaa aca gat gta aag gat tat cat att gac cag gta tca aat tta gta     2064
Lys Thr Asp Val Lys Asp Tyr His Ile Asp Gln Val Ser Asn Leu Val
        675                 680                     685

gag tct cta tca gat gaa ctc tat ctt gat gaa aag aga gaa tta ttc     2112
Glu Ser Leu Ser Asp Glu Leu Tyr Leu Asp Glu Lys Arg Glu Leu Phe
    690                 695                     700

gag ata gtt aaa tac gcg aag caa atc cat att gag cgt aac atg         2157
Glu Ile Val Lys Tyr Ala Lys Gln Ile His Ile Glu Arg Asn Met
705                 710                 715

tag agc tct aga gga tcc cgg ca                                      2180
***>Ser Ser Arg Gly Ser Arg Xxx>
```

Figure 5E

SEQUENCE LISTING

```
(1) GENERAL INFORMATION:

   (iii) NUMBER OF SEQUENCES: 2


(2) INFORMATION FOR SEQ ID NO:1:

     (i) SEQUENCE CHARACTERISTICS:
          (A) LENGTH: 2180 base pairs
          (B) TYPE: nucleic acid
          (C) STRANDEDNESS: single
          (D) TOPOLOGY: linear

    (ii) MOLECULE TYPE: cDNA

    (vi) ORIGINAL SOURCE:
          (A) ORGANISM: Bacillus thuringiensis
          (B) STRAIN: BtC-18

    (ix) FEATURE:
          (A) NAME/KEY: CDS
          (B) LOCATION: 1..2160

    (xi) SEQUENCE DESCRIPTION: SEQ ID NO:1:

ATG AAA CTA AAG AAT CCA GAT AAG CAT CAA ACG TTG TCT AGC AAT GCG       48
Met Lys Leu Lys Asn Pro Asp Lys His Gln Thr Leu Ser Ser Asn Ala
  1               5                  10                  15

AAG GTA GAT AAA ATC GCG ACG GAT TCA CTA AAA AAT GAA ACA GAT ATA       96
Lys Val Asp Lys Ile Ala Thr Asp Ser Leu Lys Asn Glu Thr Asp Ile
             20                  25                  30

GAA TTG AAA AAT ATG AAT AAT GAA GAT TAT TTG AGA ATG TCT GAG CAT      144
Glu Leu Lys Asn Met Asn Asn Glu Asp Tyr Leu Arg Met Ser Glu His
         35                  40                  45

GAG AGT ATT GAT CCG TTT GTT AGT GCA TCA ACA ATT CAA ACG GGT ATT      192
Glu Ser Ile Asp Pro Phe Val Ser Ala Ser Thr Ile Gln Thr Gly Ile
     50                  55                  60

GGA ATT GCT GGT AAG ATT CTT GGT ACT CTA GGC GTT CCT TTT CCT GGA      240
Gly Ile Ala Gly Lys Ile Leu Gly Thr Leu Gly Val Pro Phe Pro Gly
 65                  70                  75                  80

CAA ATA GCT AGC CTC TAT AGT TTT ATC TTA GGC GAG CTT TGG CCT AAG      288
Gln Ile Ala Ser Leu Tyr Ser Phe Ile Leu Gly Glu Leu Trp Pro Lys
                 85                  90                  95

GGG AAA AGT CAA TGG GAA ATC TTT ATG GAA CAT GTA GAA GCG ATT ATT      336
Gly Lys Ser Gln Trp Glu Ile Phe Met Glu His Val Glu Ala Ile Ile
            100                 105                 110

AAT CGA AAA ATA TCA ACT TAT GCA AGA AAT AAA GCA CTT ACG GAC TTG      384
Asn Arg Lys Ile Ser Thr Tyr Ala Arg Asn Lys Ala Leu Thr Asp Leu
        115                 120                 125

AAA GGA TTA GGA GAT GCC TTA GCT GTC TAC CAT GAA TCG CTT GAA AGT      432
Lys Gly Leu Gly Asp Ala Leu Ala Val Tyr His Glu Ser Leu Glu Ser
    130                 135                 140

TGG GTT GGA AAT CGT AAT AAC ACT CGA GCG AGG AGT GTA GTC AAG AAC      480
Trp Val Gly Asn Arg Asn Asn Thr Arg Ala Arg Ser Val Val Lys Asn
145                 150                 155                 160

CAA TAT ATC GCA TTA GAA CTG ATG TTT GTT CAA AAA CTA CCT TCT TTT      528
Gln Tyr Ile Ala Leu Glu Leu Met Phe Val Gln Lys Leu Pro Ser Phe
                165                 170                 175

GCA GTA TCT GGT GAG GAA GTA CCA TTA TTA CCG ATA TAT GCC CAA GCT      576
Ala Val Ser Gly Glu Glu Val Pro Leu Leu Pro Ile Tyr Ala Gln Ala
            180                 185                 190

GCC AAT TTA CAT TTG TTG TTA TTA AGA GAT GCA TCT ATT TTT GAA AAG      624
Ala Asn Leu His Leu Leu Leu Leu Arg Asp Ala Ser Ile Phe Glu Lys
        195                 200                 205
```

-continued

```
AAT GGG GGA TTA TCA GCT TCA GAA ATT TCA ACA TTT TAT AAC CGT CAA       672
Asn Gly Gly Leu Ser Ala Ser Glu Ile Ser Thr Phe Tyr Asn Arg Gln
    210                 215                 220

GTC GAA CGA ACA AGA GAT TAT TCC TAC CAT TGT GTG AAA TGG AAT AAT       720
Val Glu Arg Thr Arg Asp Tyr Ser Tyr His Cys Val Lys Trp Asn Asn
225                 230                 235                 240

ACA GGC CTA AAT AAC TTG AGG GCT ACA AAT GGC CAA AGT TGG GTT CGT       768
Thr Gly Leu Asn Asn Leu Arg Ala Thr Asn Gly Gln Ser Trp Val Arg
                245                 250                 255

TAT AAT CAA TTT CGT AAA GAT ATC GAG TTA ATG GTA TTA GAT TTA GTT       816
Tyr Asn Gln Phe Arg Lys Asp Ile Glu Leu Met Val Leu Asp Leu Val
            260                 265                 270

CGC GTA TTC CCA AGC TAT GAT ACA CTT GTA TAT CCT ATT AAA ACC ACT       864
Arg Val Phe Pro Ser Tyr Asp Thr Leu Val Tyr Pro Ile Lys Thr Thr
        275                 280                 285

TCA CAA CTT ACA AGA GAA GTA TAT ACA GAC GCA ATT GGG ACC GTC GAT       912
Ser Gln Leu Thr Arg Glu Val Tyr Thr Asp Ala Ile Gly Thr Val Asp
    290                 295                 300

CCG AAT CAA GCT CTT CGA AGT ACG ACT TGG TAT AAT AAT AAT GCA CCT       960
Pro Asn Gln Ala Leu Arg Ser Thr Thr Trp Tyr Asn Asn Asn Ala Pro
305                 310                 315                 320

TCG TTC TCT GCC ATA GAG GCT GCT GTT ATC CGA AGT CCA CAC CTA CTT      1008
Ser Phe Ser Ala Ile Glu Ala Ala Val Ile Arg Ser Pro His Leu Leu
                325                 330                 335

GAT TTT CTA GAA AAA GTT ACA ATT TAC AGC TTA TTA AGT CGG TGG AGT      1056
Asp Phe Leu Glu Lys Val Thr Ile Tyr Ser Leu Leu Ser Arg Trp Ser
            340                 345                 350

AAT ACT CAG TAT ATG AAT ATG TGG GGA GGA CAT AGA CTT GAA TCC CGC      1104
Asn Thr Gln Tyr Met Asn Met Trp Gly Gly His Arg Leu Glu Ser Arg
        355                 360                 365

CCA ATA GGA GGG GCA TTA AAT ACC TCA ACA CAA GGA TCT ACC AAT ACT      1152
Pro Ile Gly Gly Ala Leu Asn Thr Ser Thr Gln Gly Ser Thr Asn Thr
    370                 375                 380

TCG ATT AAT CCA GTA ACA TTA CAG TTC ACG TCT CGA GAC TTC TAT AGG      1200
Ser Ile Asn Pro Val Thr Leu Gln Phe Thr Ser Arg Asp Phe Tyr Arg
385                 390                 395                 400

ACT GAA TCA TGG GCA GGG CTG AAT TTA TTT TTA ACT CAA CCT GTT AAT      1248
Thr Glu Ser Trp Ala Gly Leu Asn Leu Phe Leu Thr Gln Pro Val Asn
                405                 410                 415

GGA GTG CCT AGA GTT GAT TTC CAT TGG AAA TTT CCC ACG CTA CCA ATA      1296
Gly Val Pro Arg Val Asp Phe His Trp Lys Phe Pro Thr Leu Pro Ile
            420                 425                 430

GCA TCT GAT AAT TTT TAT TAT CTA GGG TAT GCT GGA GTT GGT ACG CAA      1344
Ala Ser Asp Asn Phe Tyr Tyr Leu Gly Tyr Ala Gly Val Gly Thr Gln
        435                 440                 445

TTA CAA GAT TCA GAA AAT GAA TTA CCA CCT GAA ACA ACA GGA CAG CCA      1392
Leu Gln Asp Ser Glu Asn Glu Leu Pro Pro Glu Thr Thr Gly Gln Pro
    450                 455                 460

AAT TAT GAA TCA TAT AGT CAT AGA TTA TCC CAT ATA GGA CTC ATT TCA      1440
Asn Tyr Glu Ser Tyr Ser His Arg Leu Ser His Ile Gly Leu Ile Ser
465                 470                 475                 480

GGA TCC CAC GTG AAA GCA TTG GTA TAT TCT TGG ACA CAT CGT AGT GCA      1488
Gly Ser His Val Lys Ala Leu Val Tyr Ser Trp Thr His Arg Ser Ala
                485                 490                 495

GAT CGT ACA AAT ACA ATT GAG CCA AAT AGC ATT ACA CAA ATA CCA TTA      1536
Asp Arg Thr Asn Thr Ile Glu Pro Asn Ser Ile Thr Gln Ile Pro Leu
            500                 505                 510

GTA AAA GCG TTC AAT CTG TCT TCA GGT GCC GCT GTA GTG AGA GGA CCA      1584
Val Lys Ala Phe Asn Leu Ser Ser Gly Ala Ala Val Val Arg Gly Pro
        515                 520                 525
```

-continued

```
GGA TTT ACA GGT GGG CAT ATC CTT CGA AGA ACG AAA TCT GGT ACA TTT     1632
Gly Phe Thr Gly Gly His Ile Leu Arg Arg Thr Lys Ser Gly Thr Phe
    530                 535                 540

GGG CAT ATA CGA GTA AAT ATT AAT CCA CCA TTT GCT CAA AGA TAT CGC     1680
Gly His Ile Arg Val Asn Ile Asn Pro Pro Phe Ala Gln Arg Tyr Arg
545                 550                 555                 560

GTG AGG ATG TCC TAT GCT TCT ACT ACA GAT TTA CAA TTC CAT ACG TCA     1728
Val Arg Met Ser Tyr Ala Ser Thr Thr Asp Leu Gln Phe His Thr Ser
                565                 570                 575

ATT AAC GGT AAA GCT ATT AAT CAA GGT AAT TTT TCA GCA ACT ATG AAT     1776
Ile Asn Gly Lys Ala Ile Asn Gln Gly Asn Phe Ser Ala Thr Met Asn
            580                 585                 590

AGA GGA GAG GAC TTA GAC TAT AAA ACC TTT AGA ACT GTA GGC TTT ACC     1824
Arg Gly Glu Asp Leu Asp Tyr Lys Thr Phe Arg Thr Val Gly Phe Thr
        595                 600                 605

ACT CCA TTT AGC TTT TCA GAT GTA CAA AGT ACA TTC ACA ATA GGT GCT     1872
Thr Pro Phe Ser Phe Ser Asp Val Gln Ser Thr Phe Thr Ile Gly Ala
    610                 615                 620

TGG AAC TTC TCT TCA GGT AAC GAA GTT TAT ATA GGT CGA ATT GAA TTT     1920
Trp Asn Phe Ser Ser Gly Asn Glu Val Tyr Ile Gly Arg Ile Glu Phe
625                 630                 635                 640

GTT CCG GTA GAA GTA ACA TAT GAG GCA GAA TAT GAT TTT GAA AAA GCG     1968
Val Pro Val Glu Val Thr Tyr Glu Ala Glu Tyr Asp Phe Glu Lys Ala
                645                 650                 655

CAA GAG AAG GTT ACT GCA CTG TTT ACA TCT ACG AAT CCA AGA GGA TTA     2016
Gln Glu Lys Val Thr Ala Leu Phe Thr Ser Thr Asn Pro Arg Gly Leu
            660                 665                 670

AAA ACA GAT GTA AAG GAT TAT CAT ATT GAC CAG GTA TCA AAT TTA GTA     2064
Lys Thr Asp Val Lys Asp Tyr His Ile Asp Gln Val Ser Asn Leu Val
        675                 680                 685

GAG TCT CTA TCA GAT GAA CTC TAT CTT GAT GAA AAG AGA GAA TTA TTC     2112
Glu Ser Leu Ser Asp Glu Leu Tyr Leu Asp Glu Lys Arg Glu Leu Phe
    690                 695                 700

GAG ATA GTT AAA TAC GCG AAG CAA ATC CAT ATT GAG CGT AAC ATG TAG     2160
Glu Ile Val Lys Tyr Ala Lys Gln Ile His Ile Glu Arg Asn Met  *
705                 710                 715                 720

AGCTCTAGAG GATCCCGGCA                                               2180
```

(2) INFORMATION FOR SEQ ID NO:2:

(i) SEQUENCE CHARACTERISTICS:
(A) LENGTH: 719 amino acids
(B) TYPE: amino acid
(D) TOPOLOGY: linear (ii) MOLECULE TYPE: protein (xi) SEQUENCE DESCRIPTION: SEQ ID NO:2:

```
Met Lys Leu Lys Asn Pro Asp Lys His Gln Thr Leu Ser Ser Asn Ala
  1               5                  10                  15

Lys Val Asp Lys Ile Ala Thr Asp Ser Leu Lys Asn Glu Thr Asp Ile
             20                  25                  30

Glu Leu Lys Asn Met Asn Asn Glu Asp Tyr Leu Arg Met Ser Glu His
        35                  40                  45

Glu Ser Ile Asp Pro Phe Val Ser Ala Ser Thr Ile Gln Thr Gly Ile
     50                  55                  60

Gly Ile Ala Gly Lys Ile Leu Gly Thr Leu Gly Val Pro Phe Pro Gly
 65                  70                  75                  80

Gln Ile Ala Ser Leu Tyr Ser Phe Ile Leu Gly Glu Leu Trp Pro Lys
                 85                  90                  95
```

-continued

```
Gly Lys Ser Gln Trp Glu Ile Phe Met Glu His Val Glu Ala Ile Ile
            100                 105                 110

Asn Arg Lys Ile Ser Thr Tyr Ala Arg Asn Lys Ala Leu Thr Asp Leu
        115                 120                 125

Lys Gly Leu Gly Asp Ala Leu Ala Val Tyr His Glu Ser Leu Glu Ser
    130                 135                 140

Trp Val Gly Asn Arg Asn Asn Thr Arg Ala Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Glu Lys
        195                 200                 205

Asn Gly Gly Leu Ser Ala Ser Glu Ile Ser Thr Phe Tyr Asn Arg Gln
    210                 215                 220

Val Glu Arg Thr Arg Asp Tyr Ser Tyr His Cys Val Lys Trp Asn Asn
225                 230                 235                 240

Thr Gly Leu Asn Asn Leu Arg Ala Thr Asn Gly Gln Ser Trp Val Arg
                245                 250                 255

Tyr Asn Gln Phe Arg Lys Asp Ile Glu Leu Met Val Leu Asp Leu Val
            260                 265                 270

Arg Val Phe Pro Ser Tyr Asp Thr Leu Val Tyr Pro Ile Lys Thr Thr
        275                 280                 285

Ser Gln Leu Thr Arg Glu Val Tyr Thr Asp Ala Ile Gly Thr Val Asp
    290                 295                 300

Pro Asn Gln Ala Leu Arg Ser Thr Thr Trp Tyr Asn Asn Asn Ala Pro
305                 310                 315                 320

Ser Phe Ser Ala Ile Glu Ala Ala Val Ile Arg Ser Pro His Leu Leu
                325                 330                 335

Asp Phe Leu Glu Lys Val Thr Ile Tyr Ser Leu Leu Ser Arg Trp Ser
            340                 345                 350

Asn Thr Gln Tyr Met Asn Met Trp Gly Gly His Arg Leu Glu Ser Arg
        355                 360                 365

Pro Ile Gly Gly Ala Leu Asn Thr Ser Thr Gln Gly Ser Thr Asn Thr
    370                 375                 380

Ser Ile Asn Pro Val Thr Leu Gln Phe Thr Ser Arg Asp Phe Tyr Arg
385                 390                 395                 400

Thr Glu Ser Trp Ala Gly Leu Asn Leu Phe Leu Thr Gln Pro Val Asn
                405                 410                 415

Gly Val Pro Arg Val Asp Phe His Trp Lys Phe Pro Thr Leu Pro Ile
            420                 425                 430

Ala Ser Asp Asn Phe Tyr Tyr Leu Gly Tyr Ala Gly Val Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Gly Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525
```

-continued

```
Gly Phe Thr Gly Gly His Ile Leu Arg Arg Thr Lys Ser Gly Thr Phe
    530                 535                 540

Gly His Ile Arg Val Asn Ile Asn Pro Pro Phe Ala Gln Arg Tyr Arg
545                 550                 555                 560

Val Arg Met Ser Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Ser Asp Val Gln Ser Thr Phe Thr Ile Gly Ala
    610                 615                 620

Trp Asn Phe Ser Ser Gly Asn Glu Val Tyr Ile Gly Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Leu Tyr Leu Asp Glu Lys Arg Glu Leu Phe
    690                 695                 700

Glu Ile Val Lys Tyr Ala Lys Gln Ile His Ile Glu Arg Asn Met
705                 710                 715                 720
```

*BACILLUS THURINGIENSIS* ISOLATES WITH BROAD SPECTRUM ACTIVITY

CROSS-REFERENCE TO RELATED APPLICATIONS

This application is a Continuation-In-Part of Provisional application Ser. No. 60/035,361 filed Jan. 10, 1997.

FIELD OF THE INVENTION

The present invention relates to novel *Bacillus thuringiensis* strains, to novel toxin genes, to the proteins encoded by the genes, and to the use of genes and proteins.

BACKGROUND OF THE INVENTION

*Bacillus thunringiensis* is a gram-positive soil bacterium characterized by its ability to produce crystalline inclusions during sporulation. The crystalline inclusions can, in some subspecies, account for 20 to 30 percent of the dry weight of the sporulated cell and may be composed of more than one protein. Crystals are composed primarily of a single polypeptide, a protoxin, which may also be a component of the spore coat. The protoxin genes are located mainly on large plasmids, although chromosomally encoded endotoxins have been reported.

The crystal proteins exhibit a highly specific insecticidal activity. Many *B. thuringiensis* strains with different insect host spectra have been identified. They are classified into different serotypes or subspecies based on their flagellar antigens.

The protoxin does not exhibit its insecticidal activity until after oral intake of the crystalline body. The crystal is dissolved in the intestinal juice of the target insects. In most cases, the actual target component (toxin) is released from the protoxin as a result of proteolytic cleavage caused by the action of proteases from the digestive tract of the insects. The activated toxin interacts with the midgut epithelium cells of susceptible insects.

Electrophysiological and biochemical evidence suggests that the toxins generate pores in the cell membrane, thus disrupting the osmotic balance. Consequently, the cells swell and lyse. For several *B. thuringensis* toxins, specific high-affinity binding sites have been demonstrated to exist on the midgut epithelium of susceptible insects. Nucleotide sequences have been recorded for a large number of *B. thuringiensis* (Bt) crystal protein genes. Several sequences are nearly identical, and have been designated as variations of the same gene. The crystal protein (Cry) genes specify a family of related insecticidal proteins. The genes are divided into major classes and subclasses characterized by both the structural similarities and the insecticidal spectra of the encoded proteins. The classification, explained by Höfte and Whiteley (1989) Microbiol. Rev., 53:242–255, placed the known insecticidal crystal proteins into four major classes. The four major classes were Lepidoptera-specific (I), Lepidoptera- and Diptera-specific (II), Coleoptera-specific (III), and Diptera-specific (IV) genes. Additional classes have since been added.

The Cry1 genes are undoubtedly the best-studied crystal proteins. The Cry1 proteins are typically produced as 130 to 140 kDa protoxin proteins which are proteolitically cleaved to produce active toxin proteins about 60 to 70 Kda. The active portion or toxic domain is localized in the N-terminal half of the protoxin. Six groups of Cry1 proteins were known in 1989 when the Höfte and Whiteley article was published. These groups were designated IA(a), IA(b), IA(c), IB, IC, and ID. Since 1989, additional proteins have been discovered and classified as Cry1E, Cry1F, Cry1G, Cry1H, and Cry1X.

The spectrum of insecticidal activity of an individual protoxin from Bt tends to be quite narrow. That is, a given crystal protein is active against only a few insects. None of the crystal proteins active against Coleopteran larvae such as colorado potato beetle (*Leptinotarsa decemlineata*) or yellow mealworm (*Tenebrio molitor*) have demonstrated significant effects on members of the genus Diabrotica particularly *D. virgifera virgifera*, the western corn rootworm (WCRW) or *D. longicornis barberi*, the northern corn rootworm.

Insect pests are a major factor in the loss of the world's commercially important agricultural crops. Broad spectrum chemical pesticides have been used extensively to control or eradicate pests of agricultural importance. However, there is substantial interest in developing effective alternative pesticides.

Microbial pesticides have played an important role as alternatives to chemical pest control. The most extensively used microbial product is based on the bacterium *Bacillus thuringiensis*. However, as noted above, the majority of Bt strains have a narrow range of activity. There is therefore needed microbial strains with a broad range of insecticidal activity for use as broad spectrum insecticides and as a source for additional toxin genes and proteins.

SUMMARY OF THE INVENTION

A broad spectrum Bacillus strain is provided. The strain is active against insects from at least the orders Lepidoptera, Diptera, and Coleoptera. Additionally, the strain is active against nematodes, and rootworms. Disclosed in this invention is the isolation and partial purification of the crystal protein complex from this strain. The crystal protein complex is demonstrated to be active against rootworms and other pests. Genes, proteins, and their use, as well as the use of the strain are provided. The complete nucleotide sequence of a Cry5-like gene herein designated as Cry1I which was isolated from this strain is also provided.

The methods and compositions of the invention may be used in a variety of systems for controlling pests, particularly plant pests.

DESCRIPTION OF THE FIGURES

FIG. 1B shows an electron micrograph with the different kinds of crystal shapes as indicated by the arrows or arrow heads. The three types of crystal shapes may correlate with the three kinds of insecticidal activity toward at least three insect orders, namely: Lepidoptera, Diptera and Coleoptera.

In FIG. 4A: Lane a contains DNA molecular weight standards; Lane b, *B. thuringiensis* subsp. kurstaki; Lane c, BtC-18; Lane d: *B. thuringiensis* subsp. israelensis; Lane e, BtC-18. In FIG. 4B: Lane a contains DNA standards; Lane f, *Bacillus thuringiensis* subsp. tenebrionis; Lane g, BtC-18. The results show that BtC-18 produced the same PCR product profile as *B. thuringiensis* subsp. kurstaki, but different PCR products with Dipteran and Coleopteran DNA primers.

FIGS. 5A–5E. Nucleotide and amino acid sequence of the Cry1I gene isolated from BtC-18. See also SEQ ID NOS 1 & 2 respectively.

DETAILED DESCRIPTION OF THE INVENTION

Figure 1A:
FIGS. 1A–1B FIG. 1A shows an electron micrograph with a light micrograph insert.

Compositions and methods for controlling plant pests are provided. In particular, novel broad spectrum Bacillus strains having a wide range of insecticidal activity are provided. The strains are useful as insecticidal agents. In addition, the crystal protein complex from one of these strains has been purified and is shown to be have insecticidal properties. Methods of its purification are discussed and evidence of its activity against rootworm is disclosed. Also disclosed is the entire nucleotide sequence of a Cry5-like gene herein designated as Cry1I which was isolated from this strain.

The Bacillus strain of the invention has a broad spectrum of activity. By broad spectrum it is intended that the strains are active against insects from more than one order, preferably against insects from several orders, more preferably active against insects from at least three orders. Additionally, the strains are active against noninsect pests. For purposes of the present invention, pests include but are not limited to insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

In one embodiment, the invention encompasses the Bt isolate known as BtC-18, deposited Dec. 31, 1996 as ATCC (10801 University Blvd., Manassas, Va. 20110-2209, USA) Accession No. 55922. Protein toxins, and DNA which encodes the protein toxins are additionally encompassed. The subject invention also includes variants of the Bt isolate which have substantially the same pesticidal properties as the exemplified isolate. These variants include mutants and recombinant isolates. Procedures for making mutants are well known in the art and include ultraviolet light and nitrosoguanidine.

The *Bacillus thuringiensis* isolate C-18 produces more than one kind of crystal protein during sporulation. Microscopic examination of the sporulated cells revealed at least three different shapes of crystals: bipyrmidal similar to the lepidopteran-specific *B. thuringiensis* subsp. kurstaki; circular or irregular as that produced by dipteran-specific *B. thuringiensis* subsp. israelensis; and rhomboid-shaped similar to the coleopteran-specific *B. thuringiensis* subsp. tenebrionis.

The presence of the different types of crystals indicated that the bacterium can kill insects belonging to more than one order of insects. Bioassays confirmed that conclusion. The spore-crystal complex of C-18 killed insects from at least three orders, Lepidoptera, Diptera, and Coleoptera. Generally, Bt's produce only a single crystal and therefore have limited insect activity. Of the Bt's which have been reported to kill insects from two orders, the activity is not stable. In contrast, the present Bt has been shown to be highly stable.

Of particular interest is the corn rootworm activity exhibited by the Bacillus strains of the invention. Generally, Bt's have little or no rootworm activity. In contrast, the present strain exhibits substantial rootworm activity. By substantial activity is intended that the protein is capable of killing the target insect when present in at least microgram ($\mu$g) quantities.

Methods are available in the art for the identification and isolation of the protein or proteins associated with insecticidal activity, i.e., rootworm activity. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example, Ausubel et al. (1988) *Current Protocols in Molecular Biology, Vols.* 1 & 2, (eds.) John Wiley & Sons, NY.

Additionally, antibodies can be prepared against substantially pure preparations of the protein. See, for example, Radka et al. (1983) *J. Immunol.*, 128:2804; and Radka et al. (1984) *Immunogenetics*, 19:63. Any combination of methods may be utilized to purify protein having pesticidal properties, particularly rootworm activity. As the protocol is being formulated, insecticidal activity is determined after each purification step to assure the presence of the toxin of interest.

Methods are available in the art to assay for insect activity. Generally, the protein is mixed and used in feeding assays. See, for example Marrone et al. (1985) *J. of Economic Entomology*, 78:290–293.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J.*

*Biol. Chem.*, 257:9751–9758; Liu et al. (1983) *Int. J. Pept. Protein Res.*, 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequencers. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

Similar protocols can be utilized to isolate nematode active proteins, rootworm active proteins, or proteins having activity to other pests.

It is recognized that the pesticidal proteins may be oligomeric and will vary in molecular weight, number of protomers, component peptides, activity against particular pests, and in other characteristics. However, by the methods set forth herein, proteins active against a variety of insects or pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the active rootworm proteins, and other insecticidal and pesticidal proteins, as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing so, one skilled in the art will appreciate that the effect will be evaluated by routine screening assays.

The proteins or other component polypeptides described herein may be used alone or in combination. That is, several proteins may be used to control different insect pests.

The pesticidal proteins of the invention can be used in combination with Bt toxins or other insecticidal proteins to increase insect target range. Other insecticidal principles include protease inhibitors (both serine and cysteine types), lectins, $\alpha$-amylase and peroxidase. This co-expression of more than one insecticidal principle in the same transgenic plant can be achieved by genetically engineering a plant to contain and express all the genes necessary. Alternatively, separate plants can be transformed with different components. By crossing the plants, progeny are obtained which express all of the genes of interest.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from other Bacillus strains and organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

In this manner, the insecticidal genes of the present invention include those coding for proteins homologous to, and having essentially the same biological properties as, the insecticidal genes disclosed herein, and particularly the rootworm active gene. This definition is intended to encompass natural allelic variations in the genes. Cloned genes of the present invention can be of other species of origin. Thus, DNAs which hybridize to the present insecticidal genes are also an aspect of this invention. Conditions which will permit other DNAs to hybridize to the DNA disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SDS and 1× SSPE at 42° C., respectively, to DNA encoding the insecticidal genes disclosed herein in a standard hybridization assay. See J. Sambrook et al., Molecular Cloning, A Laboratory Manual (2d Ed. 1989)(Cold Spring Harbor Laboratory)). In general, sequences which code for insecticidal protein and hybridize to the insecticidal gene disclosed herein will be at least 75% homologous, 85% homologous, and even 95% homologous or more with the sequences. Further, DNAs which code for insecticidal proteins, or sequences which code for an insecticidal protein coded for by a sequence which hybridizes to the DNAs which code for insecticidal genes disclosed herein, but which differ in codon sequence from these due to the degeneracy of the genetic code, are also an aspect of this invention. The degeneracy of the genetic code, which allows different nucleic acid sequences to code for the same protein or peptide, is well known in the literature. See, e.g., U.S. Pat. No. 5 4,757,006 to Toole et al. at Col. 2, Table 1.

The hybridization probes may be cDNA fragments or oligonucleotides, and may be labeled with a detectable group as discussed hereinbelow. Pairs of probes which will serve as PCR primers for the insecticidal gene or a protein thereof may be used in accordance with the process described in U.S. Pat. Nos. 4,683,202 and 4,683,195.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example, EPA 0359472; EPA 0385962; WO 91/16432; Perlak et al. (1991) *Proc. Natl. Acad. Sci. USA*, 88:3324–3328; and Murray et al. (1989) *Nucleic Acids Research* 17:477–498. In this manner, the genes can be synthesized utilizing plant preferred codons. That is the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray et al. (1989) *Nucleic Acids Research*, 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) *Gene*, 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence.

Methodologies for the construction of plant expression cassettes are described in the art. The construct may include any necessary regulators such as terminators, (Guerineau et al. (1991) *Mol. Gen. Genet.*, 226:141–144; Proudfoot (1991) *Cell*, 64:671–674; Sanfacon et al. (1991) *Genes Dev.*, 5:141–149; Mogen et al. (1990) *Plant Cell*, 2:1261–1272; Munroe et al. (1990) *Gene*, 91:151–158; Ballas et al. (1989) *Nucleic Acids Res.*, 17:7891–7903; Joshi et al. (1987) *Nucleic Acid Res.*, 15:9627–9639); plant translational consensus sequences (Joshi, C. P. (1987) Nucleic Acids Research, 15:6643–6653), enhancers, introns (Luehrsen and Walbot (1991) *Mol. Gen. Genet.*, 225:81–93) and the like, operably linked to the nucleotide sequence. It may be beneficial to include 5' leader sequences in the expression cassette construct. Such leader sequences can act to enhance translation. See, for example, (Elroy-Stein et al. (1989) *PNAS USA*, 86:6126–6130), Allison et al. (1986), Macejak and Sarnow (1991) *Nature*, 353:90–94, Jobling and Gehrke (1987) *Nature*, 325:622–625, Gallie et al. (1989) *Molecular Biology of RNA*, pp. 237–256, Lommel et al. (1991) *Virology*, 81:382–385, and Della-Cioppa et al. (1987) *Plant Physiology*, 84:965–968.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA*, 88:3324–3328; Murray et al. (1989) *Nucleic Acids Research*, 17:477–498; and WO 91/16432.

For tissue specific expression, the nucleotide sequences of the invention can be operably linked to tissue specific promoters.

Methods are available in the art for the introduction and stable incorporation of the expression cassettes into plants. Suitable methods of transforming plant cells include microinjection (Crossway et al. (1986) *Biotechniques*, 4:320–334), electroporation (Riggs et al. (1986) *Proc. Natl. Acad. Sci. USA*, 83:5602–5606, Agrobacterium mediated transformation (Hinchee et al. (1988) *Biotechnology*, 6:915–921), direct gene transfer (Paszkowski et al. (1984) *EMBO J.*, 3:2717–2722), and ballistic particle acceleration (see, for example, Sanford et al., U.S. Pat. No. 4,945,050; WO91/10725 and McCabe et al. (1988) *Biotechnology*, 6:923–926). Also see, Weissinger et al. (1988) *Annual Rev. Genet.*, 22:421–477; Sanford et al. (1987) *Particulate Science and Technology*, 5:27–37 (onion); Christou et al. (1988) *Plant Physiol.* 87:671–674 (soybean); McCabe et al. (1988) *Bio/Technology*, 6:923–926 (soybean); Datta et al. (1990) *Biotechnology*, 8:736–740 (rice); Klein et al. (1988) *Proc. Natl. Acad. Sci. USA*, 85:4305–4309 (maize); Klein et al. (1988) *Biotechnology*, 6:559–563 (maize); WO91/10725 (maize); Klein et al. (1988) *Plant Physiol.*, 91:440–444 (maize); Fromm et al. (1990) *Biotechnology*, 8:833–839; and Gordon-Kamm et al. (1990) *Plant Cell*, 2:603–618 (maize); Hooydaas-Van Slogteren & Hooykaas (1984) *Nature* (*London*), 311:763–764; Bytebier et al. (1987) *Proc. Natl. Acad. Sci. USA*, 84:5345–5349 (Liliaceae); De Wet et al. (1985) In *The Experimental Manipulation of Ovule Tissues*, ed. G. P. Chapman et al. pp. 197–209. Longman, N.Y. (pollen); Kaeppler et al. (1990) *Plant Cell Reports*, 9:415–418; and Kaeppler et al. (1992) *Theor. Appl. Genet.*, 84:560–566 (whisker-mediated transformation); D'Halluin et al. (1992) *Plant Cell*, 4:1495–1505 (electroporation); Li et al. (1993) *Plant Cell Reports*, 12:250–255 and Christou and Ford (1995) *Annals of Botany*, 75:407–413 (rice); Osjoda et al. (1996) *Nature Biotechnology*, 14:745–750 (maize via *Agrobacterium tumefaciens*); all of which are herein incorporated by reference.

Alternatively, the plant plastid can be transformed directly. Stable transformation of plastids have been reported in higher plants, see, for example, Svab et al. (1990) *Proc. Nat'l. Acad. Sci. USA*, 87:8526–8530; Svab & Maliga (1993) *Proc. Nat'l Acad. Sci. USA*, 90:913–917; Staub & Maliga (1993) *EMBO J.*, 12:601–606. The method relies on particular gun delivery of DNA containing a selectable marker and targeting of the DNA to the plastid genome through homologous recombination. Additionally, plastid transformation can be accomplished by trans-activation of a silent plastid-borne transgene by tissue-specific expression of a nuclear-encoded and plastid-directed RNA polymerase. Such a system has been reported in McBride et al. (1994) *Proc. Natl. Acad. Sci., USA*, 91:7301–7305.

The cells which have been transformed may be grown into plants in accordance with conventional ways. See, for example, McCormick et al. (1986) *Plant Cell Reports*, 5:81–84 (1986). These plants may then be grown, and either pollinated with the same transformed strainer or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A number of methods are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

General methods for employing the strains of the invention in pesticide control or in engineering other organisms as pesticidal agents are known in the art. See, for example U.S. Pat. No. 5,039,523 and EP 0480762A2.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bacteriocides, nematocides, mollusocides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

The following experiments are offered by way of illustration and not by way of limitation.

EXPERMENTAL

Introduction

*Bacillus thuringiensis* (Bt) strain C-18 is a gram-positive sporeforming bacterium that produces parasporal crystals which have multiple toxicity against three orders of insects: Lepidoptera, Coleoptera and Diptera as well as to nematodes. C-18 is unique because of its capacity to kill such a wide range of agriculturally and biomedically important pests. No other Bt strain or isolate has been reported to have such a wide host range. The vast majority of Bt's can kill insects belonging to only one order of insects.

Isolation

C-18 was isolated in Egypt from dead pink bollworm larvae harvested from cotton bolls grown in cotton fields in Egypt. Standard bacteriological procedures were used to isolate gram-positive, spore forming bacteria. The larvae were washed twice with sterile deionized water, transferred to fresh sterile water (1 ml), macerated with a sterile glass-rod before being subjected to a heat treatment (5 min. at 100° C.). The heat treatment killed all the vegetative and non-sporulating microbes. 100 ul samples were then streaked onto LB-agar plates and incubated at 30° C. overnight. Individual colonies were then picked, streaked onto fresh sporulating medium and incubated at 30° C. for 48 hours.

The resulting colonies were stained with endospore stain and examined microscopically. All standard bacteriological techniques including physiological and biochemical reactions were employed to determine the identity of the isolates and only those which matched *Bacillus thuringiensis* (Bt) were subjected to detailed analysis and evaluation. Among the isolates selected for determining insecticidal and nematocidal activities was C-18.

Figure 1B:
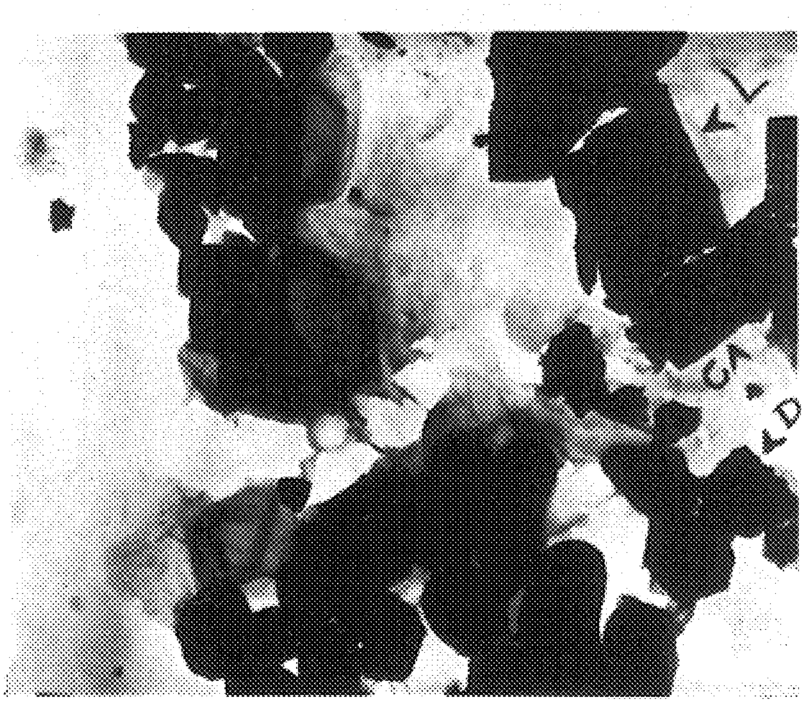

A unique aspect of the isolate C-18 was its ability to produce more than one kind of protein crystal during sporulation. Microscopic examination of the stained sporulated cells revealed at least three different shapes of crystals: bipyrimidial similar to the lepidopteran-specific *B. thuringiensis* subsp. kurstaki; circular or irregular as that produced by *B. thuringiensis* subsp. israelensis; and, rhomboid-shaped similar to the *B. thuringiensis* subsp. tenebrionis (FIG. 1 A&B).

Insect & Nematode Bioassays

The insecticidal activity of C-18 was measured using bioassays involving a variety of insects that represent the Lepidoptera, Coleoptera and Diptera orders of insects. Initial insect bioassays were performed with whole bacterial cells and included the raspberry silkworm *Philosamia ricini* (Lepidopteran), the mosquito *Culex pipiens* (Dipteran), and the flour beetle Tribollium spp. (Coleopteran). Nematode bioassays were done with the tomato nematode *Melodogyne incognata*. Positive results from these bioassays Table 1 prompted a more comprehensive analysis of the insecticidal and nematocidal activities of C-18 parasporal crystals. As can be seen in Table 1, C-18 is effective against a broad spectrum of insects. Also parasporal crystals purified from C-18 exhibited the same nematocidal activity as the whole organism (FIG. 1).

A more comprehensive bioassay system using larger numbers of insects representing the three orders mentioned above was then performed.

In Table 1, bioassays were divided into three groups. Group I contains the results of the lepidopteran insects (cotton leafworm *Spodoptera littoralis*, cotton bollworm *Pectinophora gossypiella*, tobacco hornworm *Manduca sexta*, raspberry silk worm *Philosamia ricini*, and a corn borer *Sesamia cratica*). Group II includes dipteran insects (mosquitoes *Culex pipiens, Aedes aegypti, Aedes albopictus, Aedes triseriatus*, and a blue tongue virus vector: *Culicoides variipennis*). Group III represents the coleopteran insects (flour beetle Tribolliumn spp., Colorado potato beetle *Leptinotarsa decemlineata*, western corn rootworm *Diabortica virgifera* and southern corn rootworm *D. undecimpuncata howardi*).

The bacterium was also tested against the nematode *Melodogyne incognata* (FIG. 3).

TABLE 1

Pesticidal Activities of an Egyptian Isolate
*Bacillus thuringiensis* (BtC-18)

| INSECT | BtC-18 | BTK | BTI | BTT |
|---|---|---|---|---|
| Group I: Lepidopteran-insects | | | | |
| *Spodoptera littotalis*[1] | 10.00 | 40.00 | 0.0 | 0.0 |
| *Pectinophera gossypiella*[1] | 0.45 | 40.00 | 0.0 | 0.0 |
| *Manduca sexta*[1] | 0.45 | 7.00 | 0.0 | 0.0 |
| *Philosamia ricini*[1] | 0.43 | 3.00 | 0.0 | 0.0 |
| *Sessemia cratia*[1] | 20.00 | 30.00 | 0.0 | 0.0 |
| Group II: Dipteran-insects | | | | |
| *Culex pipiens*[2] | 7.00 | 0.0 | 5.50 | 0.0 |
| *Aedes aegypti*[2] | 200.00 | 0.0 | 40.00 | 0.0 |
| *Aedes albopictus*[2] | 36.00 | 0.0 | nd | 0.0 |
| *Aedes triseriatus*[2] | 360.00 | 0.0 | nd | 0.0 |
| *Culicoides variipennis*[2] | 18.00 | 0.0 | NO | 0.0 |
| Group III: Coleopteran-insects | | | | |
| *Tribollium sp.*[3] | 35.00 | 0.0 | 0.0 | 30.00 |
| Colorado Potato Beetle1 | 50.00 | 0.0 | 0.0 | 25.00 |
| Western Corn Rootworm[1] | 350.00 | 0.0 | 0.0 | 8,000.00 |
| Southern Corn Rootworm[1] | 350.00 | 0.0 | 0.0 | 10,000.00 |

[1]The LC50 is expressed in $ng/cm.^2$
[2]The LC50 is expressed in ng/ml.
[3]The LC50 is expressed in ng/g.
* BtC-18 also exhibited toxic activity against Nematodes.

Microscopic Examination of C-18

C-18 produces at least three morphological types of parasporal crystals (FIG. 1). The three types or shapes are: (i) bipyrimidal—characteristic of those crystals that are toxic to lepidopterans, (ii) rounded, amorphous clusters—characteristic of dipteran-specific crystals, and (iii) rhomboid—characteristic of coleopteran-specific crystals. Presence of these three morphological crystal types correlate with the three kinds of insecticidal activities normally associated singularly with all other Bt's described in the scientific literature.

Profile of Proteins Extracted from Vegetative & Sporulating Cells of C-18

The molecular characterization of BtC-18 was determined at the protein and the gene levels. *Bacillus thuringiensis* has two phases of growth, the vegetative phase and the sporulation phase. The bacterium produces a specific protein pool during each phase of growth. The proteins are the expression products of active genes at the specific stage of development. These proteins can be separated and visualized on a sodium dedocylsulphate-polyacrylamide gel by electrophoresis (SDS-PAGE).

Proteins of vegetative and sporulating cells of the various strains of Bt described in the literature have common and characteristic banding patterns when analyzed by SDS-polyacrylamide gel electrophoresis. To determine whether C-18 has a distinctive protein profile of its own, proteins extracted from both vegetative and sporulating cells were examined by this technique and compared with Bt subspecies kurstaki (lepidopteran-specific), israeliensis (dipteran-specific), and tenebrionsis (coleopteran-specific). C-18 does, indeed, have distinctive protein profiles when compared with several other commonly known subspecies of Bt.

Immunochemical Staining of Crystal Proteins

Western analysis of purified crystal proteins from C-18 was performed and proteins identified by this technique were compared with the same three subspecies of Bt mentioned above. Although there are some similarities among the four organisms, C-18 does exhibit a distinctive and characteristic crystal protein profile.

Plasmid DNA Profiles

Genes responsible for encoding insecticidal proteins that constitute parasporal crystals of Bt usually are associated with plasmid DNA although there is evidence that such genes are chromosomally linked as well. The plasmids purified from C-18 are displayed in FIG. 2. The plasmid profile of C-18 is distinctive when compared to the profiles of the same three subspecies of Bt indicated above.

Figure 2:
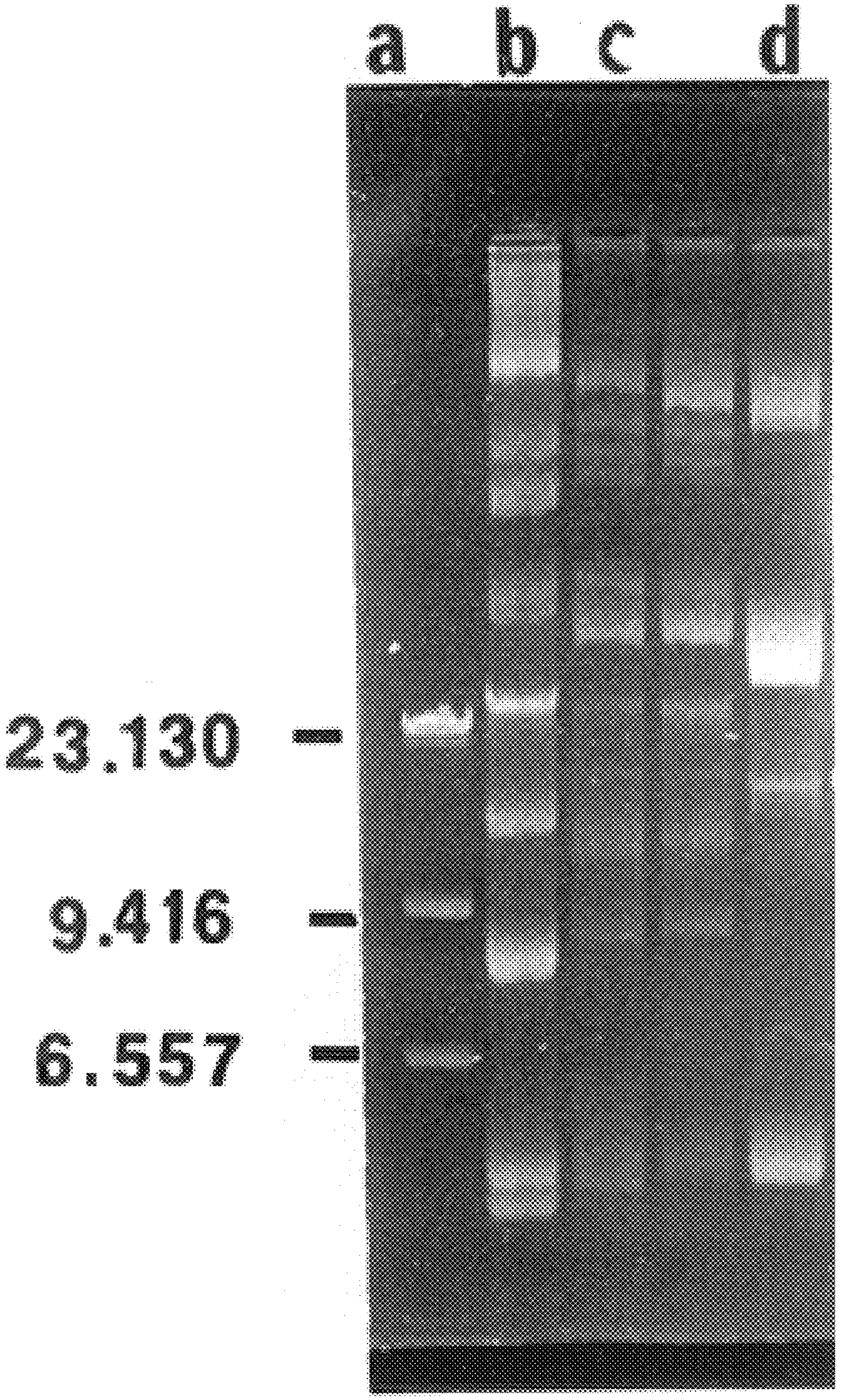
FIG. 2 Plasmid profile of BtC-18. Lane a: DNA molecular weight standards; Lane b: *B. thuringiensis* subsp. kurstaki; Lane c: *Bacillus thuringiensis* subsp. aizawia; and, Lane d: strain C-18. BtC-18 also has different plasmid DNA profiles from the other known *B. thuringiensis* subspecies, such as subspecies israelensis and tenebrionis, (data not shown).

This bacterium contains large number of plasmid DNA molecules. The majority of the toxin genes have been reported to be carried on one of the large plasmids, however, few have been reported on the chromosome of some Bts. The plasmid profile of C-18 has been used as a tool to differentiate between bacterial species. The plasmid profile of the BtC-18 was found to be different from the other subspecies of *B. thuringiensis* tested as indicated in FIG. 2.

Polymerase Chain Reaction (PCR)

Figure 4A:
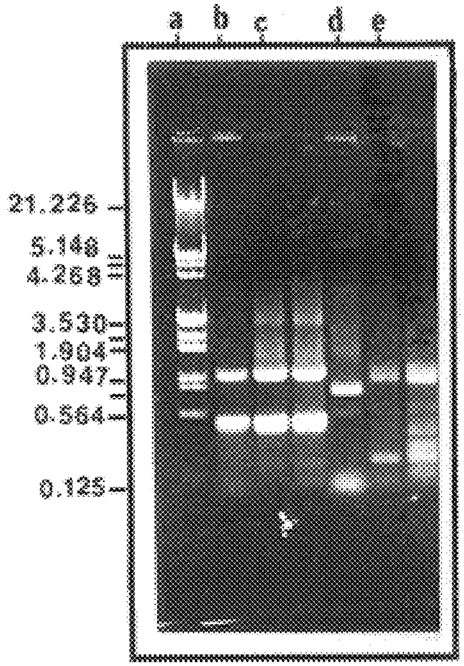
FIGS. 4A–4B PCR product profile of BtC-18.
Figure 4B:
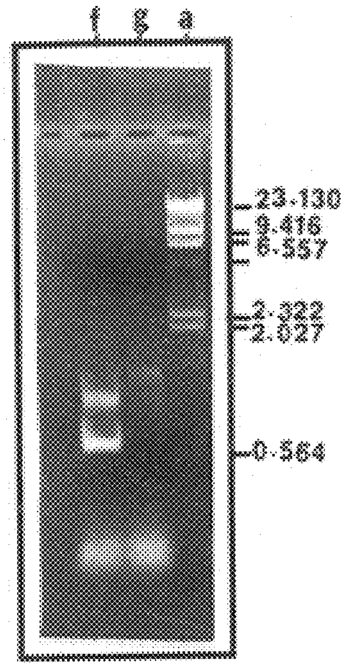

To determine the existence of genes (Cry genes) in C-18 that may encode different insecticidal proteins (Cry proteins), specific DNA primers were constructed and used in PCR analysis of C-18 genomic DNA. The primers were custom designed against conserved regions in the genomes of the same subspecies used above. Amplification of various DNA fragments revealed that C-18 contains similar Cry1 (Lepidopteran-specific) genes as Bt subsp. kurstaki but different Cry genes that those of Bt subspecies israelensis and tenebrionis (FIG. 4).

The proof of the existence or absence of the three genes encoding the three crystals produced by BtC-18 was proven by the use of specific DNA primers (three sets, each consisting of two pairs specific for one gene) designed against conserved regions in the genomes of *B. thuringiensis* subsp. kurstaki (Lep1A, Lep1B, Lep2A, and Lep2B), *B. thuringiensis* subsp. israelensis (Dip1A, Dip1B, Dip2A, and Dip2B) and *B. thuringiensis* subsp. tenebrionis (Col1A, Col1B, Col2A, and Col2B).

The primers were used in the polymerase chain reaction (PCR) to give specific product profiles. The two pairs of Lep primers amplify a 0.49 kb and a 0.908 kb DNA fragment. The Dip primers amplify a 0.797 kb and 1.290 kb DNA fragment. The Col primers amplify a 0.649 kb and 1.060 kb DNA fragments (FIG. 4).

Western blot analysis of the crystal proteins produced by BtC-18 confirm that the crystal proteins of BtC-18 are different from the subspecies israelensis and tenebrionis.

Purification of the C18 Crystal Protein Complex and Insecticidal Properties

The BtC18 crystal complex was purified from the sporulated culture broth by Renographin gradient from the methods discussed in Lee et al. (1995) *Biochem. Biophys. Res. Comm.* 126: 953–960. The purified crystals were washed several times with de-ionized water to get rid of any contaminants. The crystal complex was subjected to differential solublization at various pH's according to the methods of Dai and Gill (1993) *Insect Biochem. Molec. Biol.* 23:273–283 and Hofte et al. (1986) *Eur. J. Biochem.* 161:273–280 and fractions (F1, F2, F3, F4, F5, and F6) obtained from this procedure were bioassayed against corn rootworms (southern and western) as representative of coleopteran insects and tobacco hornworm as lepidopteran insects. All fractions killed both representative insects, but with varying degrees. Fractions F2, F4, and F6 killed rootworms very efficiently. 5 $\mu g/cm^2$ of the fractions killed 80–90% of the tested insects. 100% kill was recorded at 10 $\mu g/cm^2$. All fractions killed the tobacco hornworm albeit with variable efficiencies.

Binding of BtC18 Toxins to Specific Brush Border Membrane Proteins from the Midgut of Different Insects Brush border membrane vesicles (BBMV) were prepared from: corn rootworms (WCRW and SCRW), tobacco hornworm (MS), and European corn borer (ECB) according to methods used by Wolfersberger et al. (1987) Comp. Biochem. Physiol. 86A:301–308. Specific amounts (20-MS, 50-ECB, and 120-W/SCRW $\mu g$/lane) of BBMV's were loaded and separated by SDS-PAGE. The separated proteins were electro-blotted onto PVDF nylon membranes and were reacted with $^{125}I$ labeled fractions (F2, F4, F5, and F6) from BtC18, which bind to specific receptors from the BBMV. The radioactive membranes are then exposed on film. Where there's a band there is an interaction with the specific receptor. Evident in this analysis is the broad based interaction of F6 radiolabelled proteins with the various brush border membrane proteins extracted from these pests (Table 2). Based on this observation, F6 appears to have the largest range of activity.

TABLE 2

| BtC18 Protein | BBMV Binding Protein (kDa) | | | |
|---|---|---|---|---|
| fraction | MS | ECB | SCRW | WCRW |
| F2 | 210 | nd | nd | nd |
| P4 | 210 | nd | nd | nd |
| | 84 | nd | nd | nd |
| | 45 | nd | nd | nd |
| F5 | 210 | nd | nd | nd |
| | 120 | nd | nd | nd |
| | 60 | nd | nd | nd |
| | 55 | nd | nd | nd |
| F6 | 210 | 210 | 210 | nd |
| | 120 | 84 | nd | 180 |
| | 60 | nd | 150 | 150 |
| | 45 | nd | 50 | 50 |
| | 40 | nd | 42 | 42 |

Identification of Cry Genes

DNA primers available in the scientific literature enabled the identification of the types of genes present in this BtC-18 isolate. Some of the primers were designed to differentiate between the members of the same family of genes such as Cry1 family, Cry2 genes, Cry3 genes, Cry4 genes and Cry5 gene. These primers were used in PCR analysis to determine the number and kinds of the different genes present in the isolate BtC-18. Seceral genes were determined to be present in BtC-18. The identified genes were Cry1Aa, Cry1Ab, Cry1Ac, Cry1B, Cry1C, Cry1D, Cry2A, Cry2B, and a Cry5-like gene designated as Cry1I.

These genes can be grouped into three major families: i) Cry1 family genes encode for proteins toxic to lepidopteran insects only, Cry1Aa, Cry1Ab, Cry1Ac, Cry1C, Cry1D, ii) Cry2 genes encode proteins toxic to lepidopteran and dipteran insects, Cry2A and Cry2B, and iii) Cry1B and Cry5 genes encodes proteins toxic against lepidopterous and coleopterans insects. A pool of at least nine genes were present in this single bacterium, which covers the widest range of insecticidal activity recorded in the scientific literature.

Identification of Additional Genes with Potential Insecticidal Activity

In the same manner as the above example, additional genes were discovered to exist in BtC18 which are potentially responsible for giving this strain its broad spectrum of insecticidal activity. Cry1F, Cry1G, Cry1K, and Cry1M were found as well as nematode specific genes, designated nem1, nem3, nem5 and nem7. In addition, a vegetative toxin was discovered in BtC18 which gives a PCR generated band of the size expected for strain BtHD1. This vegetative toxin is produced during vegetative growth and kills black cut worm of corn (BCW).

Cloning of Genes

All the genes detected by PCR in BtC-18, mentioned above, were cloned into BlueScript sk+II plasmid vector. Custom made DNA primers against the toxin domains of the respective genes were used in PCR to amplify and target the N-terminus part of the genes. The amplification products were eluted from the gel, biocleaned and ligated to blunt ended pBlueScript. *E. coli* was subsequently transformed with this vector, and, recombinants containing the target genes were identified. The positive recombinants were determined using the specific DNA primers and PCR to identify the expected gene products. Recombinants clones were expressed in *E. coli* and the total cellular proteins of the recombinants were analyzed by SDS-PAGE. For better expression, the genes were cloned into an expression plasmid pTrc99.

Cry1I Gene

Analysis of the Cry1I expression products by SDS-PAGE was performed. Two proteins were produced, a 70 kDa protein and a smaller 58 to 60 kDa protein which are not produced by *E. coli* transformed with pTrc99 alone. The Cry1I gene was subcloned for the purpose of restriction mapping and DNA sequencing. Three nucleotide sequences of three different segments of the Cry1I gene from BtC-18 were obtained using the dideoxy chain termination method (sequences not shown). The three segments were the 5' and 3' ends of the gene as well as a middle segment. The nucleotide sequence of these three segments of the Cry1I gene from BtC-18 were compared using Blast server to nucleotide sequences of the published sequences of several different Cry5 genes. By this method identities and homologies of the nucleotide and amino acid sequences were determined. The closest relative to the C18 Cry1I gene is that of entomocidus. C18 Cry1I shares 97% nucleotide identity and 92% amino acid identity with the entomodidus Cry5. The complete nucleotide sequence of the C18 Cry1I has been obtained and is represented in FIG. 5 (SEQ ID NO:1).

Cry1I activity Against Rootworm

The C18 Cry1I gene was inserted into the expression vector pTrc99 with IPTG induction. *E.coli* strain BL21 was transformed with vector plus Cry1I insert and empty vector as a negative control. Once the bacteria had grown to the appropriate cell density, they were pelleted and resuspended in 11 ml of buffer (10 mM MgSO4, 0.3% Tween-20, 2 mM PMSF). The cellular suspension was sonicated and protein extracted. The concentration of the protein extract was ~45 mg/ml. WCRW (Western Corn Rootworm) larvae were challenged with various concentrations of the protein extract and mortality scored after three days. Results of this assay demonstrates a dramatic increase in WCRW mortality compared to the negative control at doses as low as 2.3 $\mu$g/cm$^2$. At these levels mortality of the larvae exposed to the extract containing Cry1Ip is up 55% compared to the mortality of the larvae unexposed. At 11.8 $\mu$g/cm$^2$ the mortality is up 80%. See Table 3. This is clear evidence that Cry1I is one of the constituents in the BtC18 insecticidal arsenal that demonstrates anti-rootworm activity.

TABLE 3

| Extract vol. | Dead (WCRW) | Live (WCRW) | % Mortality | Est. Cry1I dose ($\mu$g/cm$^2$) |
|---|---|---|---|---|
| 0.1 ml | 6 | 2 | 75 | 2.3 |
| 0.5 ml | 8 | 0 | 100 | 11.8 |
| 1.0 ml | 8 | 0 | 100 | 22.3 |
| 2.0 ml | 8 | 0 | 100 | 44.7 |
| Control | 3 | 12 | 20 | 0 |

Purification of Insecticidal Proteins from BtC-18

FPLC Separation of BtC-18 Crystal Proteins

Protein fractions from BtC-18 were dialyzed, solubilized and then purified on a Mono Q column following the FPLC procedure recommended by the manufacturer:

1. Portions of the fractions were loaded onto the column and eluted using NaCl gradients.
2. Each individual fraction was bioassayed against different insects, analyzed by SDS-PAGE, and ligand binding studies were performed using the midguts of different insects to identify specific receptor proteins.

Isolation of Crystal Proteins from BtC-18.

The bacterium BtC-18 was cultured in liquid sporulation medium (T3-medium) at 30°–32° C. and the crystal proteins were purified according to Lee et al. (1985) *Biochem. Biophys. Res. Commun.*, 126:953–960 using the following procedure:

1. The cells were grown to the spore stage. The crystal proteins were released into the medium following autolysis of the cells.
2. The spore-crystal complexes were separated by centrifugation (10,000 rpm, for 10 min at 4° C.). The complex was washed twice each with 1M potassium chloride in deionized water.
3. The pellet was resuspended in distilled water and homogenized with a Dounce homogenizer followed by centrifugation to separate the protein complexes. This step was repeated two times.
4. The pellet (2–4 g) was suspended in a 68% Renografin gradient (9.6 ml of 2% Triton X-100 and 20.4 ml of Renografin). The mixture was homogenized and subjected to sonication 10 times (20 pulses each time).
5. The mixture was centrifugated at 27,000 rpm for 15 hours. The viscous top band on the gradient contained the crystal proteins. The purity of the crystal proteins was checked by microscopic examination.
6. The crystal pellet was resuspended in 30 ml of 55% Renografin, 1% Triton X-100, homogenized with a glass Dounce homogenizer and sonicated 10 times as above.
7. The mixture was centrifugated again at 27,000 rpm for 15 h and the crystal proteins were precipitated as a white pellet.
8. The supernatant was carefully removed and the pellet was washed three times with distilled water before lyophilization.

Solubilization of the Crystal Proteins from BtC-18

Solubilization of the crystal proteins was accomplished according to the methods of Dai et al. (1993) *Insect Biochem. Mol. Biol.*, 23:273–283 and Höfte et al. (1986) *Eur. J. Biochem.*, 161:273–280.

1. 50 $\mu$g of the purified crystal proteins were dissolved in 5 ml of the following solution:
   Sodium carbonate (pH 9.5) 50 mM
   Dithiothreitol (DTT) 10 mM
   Phenylmethylsulfonyl Fluoride (PMSF) 5 mM
   Ethylenediaminctctraacetate, disodium 10 mM→

The mixture was incubated at 37° C. for 80 min. with continuous shaking.

2. The mixture was spun at 14K rpm for 15 min. and the supernatant was analyzed by SDS-PAGE.
3. The pellet was dissolved in the following solution:
   Sodium hydroxide (pH12) 50 mM
   Dithiothreitol (DTT) 10 mM
   Phenylmethylsulfonyl fluoride (PMS) 5 mM and incubated at 37° C./1 hour.
4. The supernatant was collected again by centrifugation at 14k for 15 min.
5. The fractions were dialyzed against Tris-HCl (50 mM, pH 9) containing 50 mM NaCl.

After purification, the proteins are assayed for activity against insects of interest.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleotidc sequence encoding the protein of SEQ ID NO:2 or a pesticidally active fragment thereof.

2. The nucleotide sequence of claim 1, said sequence having the sequence set forth in SEQ ID NO:1.

3. A chimeric gene comprising a promoter operable in a plant cell operably linked to a nucleotide sequence encoding the Cry1I protein, said protein having the amino acid sequence set forth in SEQ ID NO:2.

4. The chimeric gene of claim 3 wherein said nucleotide sequence encoding the Cry1I protein is the sequence set forth in SEQ ID NO:1.

5. A plant transformed with the nucleotide sequence of claim 1.

6. A plant stably transformed with the gene of claim 3.

7. A plant stably transformed with the gene of claim 4.

8. Seed of the plant of claim 5.

9. Seed of the plant of claim 6.

10. Seed of the plant of claim 7.

* * * * *

UNITED STATES PATENT AND TRADEMARK OFFICE

CERTIFICATE OF CORRECTION

PATENT NO. : 5,986,177

DATED : November 16, 1999

INVENTOR(S) : Osman et al.

It is certified that error appears in the above-identified patent and that said Letters Patent is hereby corrected as shown below:

Col. 13, Table 2, line 56, col. 1, "P4" should read -- F4 --.

Figure 3A:
FIGS. 3A–3B Protective effect of BtC-18 against the root nematode *Meloidogyne incognata*. In panel A: the roots of infected tomato plant with the nematode (positive control). panel B: the roots of tomato plants infected with nematode eggs before BtC-18 was applied, and panel C: roots of plant treated first with BtC-18 and then infected with nematode eggs.
Figure 3B:
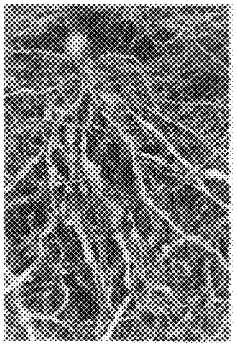
Figure 3C:
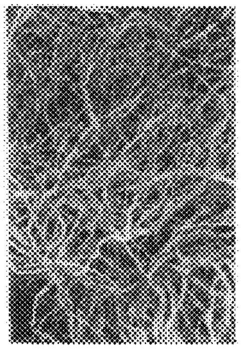

Col. 2, line 61, "FIGS. 3A-3B" should read -- FIGS. 3A-3C --.

Signed and Sealed this

Third Day of April, 2001

Attest:

Nicholas P. Godici

NICHOLAS P. GODICI

*Attesting Officer*

*Acting Director of the United States Patent and Trademark Office*